United States Patent

Pasenok et al.

Patent Number: 5,756,834
Date of Patent: May 26, 1998

[54] PROCESS FOR PREPARING FLUORINATED AROMATICS

[75] Inventors: Sergej Pasenok, Liederbach; Wolfgang Appel, Kelkheim, both of Germany

[73] Assignee: Hoechst Aktiengesellschaft, Frankfurt, Germany

[21] Appl. No.: 746,223

[22] Filed: Nov. 7, 1996

[30] Foreign Application Priority Data

Nov. 11, 1995 [DE] Germany .................. 195 42 148.5

[51] Int. Cl.$^6$ ............................................. C07C 63/04
[52] U.S. Cl. .................... 562/493; 560/103; 564/183; 570/127; 558/425; 168/437; 168/937; 168/938
[58] Field of Search .................... 562/493; 560/103; 570/127; 564/183; 568/937, 938, 437; 558/425

[56] References Cited

FOREIGN PATENT DOCUMENTS 0566268  10/1993  European Pat. Off.
2 647 106 11/1990  France.

OTHER PUBLICATIONS

F. Cacace et al., Jour. Am. Chem. Soc., vol. 102, pp. 3511–3515, 1980.
S.T. Purrington et al., Jour. Org Chem. vol. 56, 1991, pp. 142–145.
M. van der Puy, Tetrahedron Letters, vol. 28, 1987, pp. 255–258.
Chambers et al., Jour. Chem. Soc. Chem. Commun., 1995, p. 17.

*Primary Examiner*—Paul J. Killos
*Attorney, Agent, or Firm*—Frommer Lawrence & Haug LLP

[57] ABSTRACT

It is known to prepare fluorinated aromatic compounds of the formula I

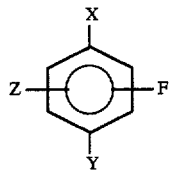

in which
X, Y and Z can have the meaning specified in the description, by reacting aromatic compounds of the formula II

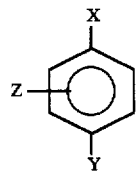

in which X, Y and Z have the meaning specified for formula I, with fluorine in a reaction medium.

According to the invention, the direct fluorination is carried out in a reaction medium containing polyfluoroalkanesulfonic acids of the formula III $$CF_nH_{3-n}(CFY)_m\text{—}SO_3H \qquad (III)$$

in which
m, n and Y have the meaning specified in the description.

By this means, it is possible, particularly advantageously to provide a process, which improves the known processes not only with regard to the selectivity and the yield, but also with respect to the quality of the resulting products of the process in a manner not readily predictable.

Fluorinated aromatic compounds of the formula I as intermediates for active compound synthesis.

13 Claims, No Drawings

PROCESS FOR PREPARING FLUORINATED AROMATICS

The invention relates to a process for preparing fluorinated aromatic compounds of the formula I

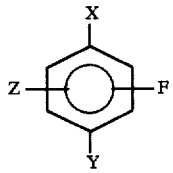

in which
X is COOH, COOR, CONH$_2$, CONR$^1$R$^2$, CF$_3$, CN, CHO, NO$_2$ or NH$_2$,
Y is F, Cl, OCH$_3$, OCF$_3$, OCCl$_3$, p-NO$_2$—C$_6$H$_4$, p-NO$_2$—C$_6$H$_4$—O or OH, and
Z is H, F, Cl, CF$_3$, CCl$_3$ or OCH$_3$,
where R, R$^1$ and R$^2$ independently of one another can be identical or different C$_1$-C$_6$-alkyl, linear or branched, and the alkyl radicals R, R$^1$ and
R$^2$ can optionally be up to trisubstituted with halogen, by reacting aromatic compounds of the formula II

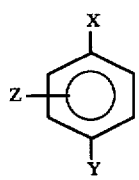

in which
X, Y and Z have the meaning specified for formula I, with fluorine in a reaction medium.

Substituting fluorine for aromatically bound hydrogen is of great importance for the synthesis of bioactive substances and for preparing precursors of such compounds.

The use of molecular fluorine for the targeted selective replacement of individual hydrogen atoms has long been restricted to only a few cases, however. The reason is, inter alia, that the fluorination of aromatics essentially proceeds via a free-radical mechanism with only low selectivity, or with the complete absence of selectivity. In this process, by-products are frequently formed by cleavage of the organic molecules and recombination of the fragments.

With regard to more details of the prior art, the publications

D1=F. Cacace et al., J. Am. Chem. Soc. 102 (1980) 3511,
D2=S. T. Purrington et al., J. Org. Chem. 56 (1991) 142,
D3=EP-A-0 566 268,
D4=M. van der Puy, Tetrahedron Lett. 28 (1987) 255, and
D5 =Chambers et al., J. Chem. Soc. Chem. Commun., 1995, page 17 are mentioned.

To reduce or avoid by-product production, for example, monosubstituted benzenes have been reacted with molecular fluorine, greatly diluted by N$_2$, at −78° C. in CCl$_3$F or CH$_3$CN (D1).

In D2, the direct fluorination of aromatic substrates of the type ΦZ, in which Z is Cl, CHO, NO$_2$, OH, NHCH$_3$, OCH$_3$ or CH$_3$, was studied with and without the addition of BCl$_3$ or AlCl$_3$. It was found that adding BCl$_3$ increased both the reaction conversion rate and the yield of para isomer.

A process for preparing 3- and 5-trifluoro-substituted aromatic compounds is subject-matter of D3. In the process described in D3, the starting materials used are aromatic compounds which have a group in the 1 position lowering the electron density and electron-donor groups in the 2 and 4 positions as groups increasing the electron density in the aromatic ring system.

D4 discloses that the direct fluorination of 4-substituted pyridines at low temperatures leads to the formation of 2-fluoro derivatives with crude yields of between 25 and 60% (weight/weight).

Recently, the authors of D5 showed that the fluorination of aromatic compounds with F$_2$ in strongly polar solvents, such as HCOOH and H$_2$SO$_4$, leads to fluorinated compounds in relatively high yields, the selectivity of the reaction being simultaneously improved. The best results, according to D5, are achieved in the direct fluorination of 1,4-disubstituted benzene derivatives of the formula IV

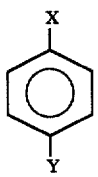

in which
X is COOH or NO$_2$, and
Y is F, Cl or OCH$_3$, using concentrated H$_2$SO$_4$ as strongly polar reaction medium.

This method is particularly suitable for aromatics having patterns of substitution which lead to further selective substitutions. These include, especially disubstituted aromatics which each contain one activating substituent and one deactivating substituent and which therefore direct into the o/p or m position.

The use of sulfuric acid as a medium for direct fluorination of aromatics has a number of serious disadvantages.

i. The solubility of aromatic compounds in concentrated sulfuric acid is generally very low. This results in the necessity of working in relatively dilute solutions (about 3–10% by weight), which is accompanied by technical disadvantages.

ii. The treatment with molecular fluorine gas requires very high fineness of gas bubbles and gas distribution. This is generally achieved by very tall reactors and multistage agitators. The reaction medium sulfuric acid, in particular, with its very high surface tension and relatively low fluorine solubility therein, requires this complex equipment, in order to consume the elemental fluorine completely. This means, de facto, long reaction times, high energy consumption and high apparatus costs.

iii. The use of sulfuric acid as the direct fluorination medium makes workup difficult. Generally, dilution of the complete reaction medium with water is necessary, in order to isolate the target products. This leads to corresponding waste water pollution.

In view of the prior art cited and discussed herein, it was therefore the object of the invention to specify a process of the generic type mentioned at the outset which permits the preparation of defined target compounds in good yield with high selectivity. The novel process is to be suitable for industrial use, pollute the environment as little as possible and simultaneously to be implemented inexpensively with relatively simple means. At the same time, the process is to be free, in particular, of the abovementioned disadvantages.

These objects and other objects not specified in more detail are achieved by a process of the type mentioned at the outset having the feature of the characterizing part of claim 1. Advantageous modifications of the process of the invention are protected in the subclaims dependent on claim 1. A use of the invention is subject-matter of claims 12 and 13.

By carrying out the direct fluorination in a reaction medium containing polyfluoroalkanesulfonic acids of the formula III $$CF_nH_{3-n}(CFY)_m—SO_3H \qquad (III)$$

in which
- m is 0 or a positive integer from the range 1 to 5, n is a positive integer from the range 1 to 3 and Y is F, Cl, H or RFY', where Y' is F, Cl or H, and
- R is $C_{1-3}$-alkylene, linear or branched, which, if appropriate, can be partially fluorinated or else perfluorinated, a process is particularly advantageously successfully provided which improves the known processes not only with regard to the selectivity and the yield, but also with respect to the quality of the resulting products of the process in a manner not readily predictable. In particular, the process of the invention has the following advantages:
  i. The solubility of aromatics is significantly better in polyfluoroalkanesulfonic acids than in sulfuric acid, which has the advantage that a 10–25% by weight solution of the aromatic substrates can be employed in the reaction medium.
  ii. At the same time, the solubility of $F_2$ in polyfluoroalkanesulfonic acids of the formula III is greater than in $H_2SO_4$, so that the elemental fluorine is completely consumed without great technical expenditure and the reaction time and energy consumption are decreased.
  iii. The reaction mixture can be worked up after the fluorinated by separation of the reaction mixture by distillation which enables the polyfluoroalkanesulfonic acids to be isolated and recycled.

The diluents or solvents used according to the invention are polyfluoroalkanesulfonic acids of the formula III. These compounds may for the most part be obtained commercially and are thus available. Compounds of the formula III, which are not commercially obtainable, may be prepared in a simple manner by processes familiar to those skilled in the art. Said reaction media can be used as diluents, solvents or as an additive to such media. The polyfluoroalkanesulfonic acids of the invention can be used in pure form or in a mixture of more than one compound.

The various compounds belonging to formula III have different boiling points. Depending on the boiling point of the aromatic starting materials and products and depending on the product workup sought, a compound of the formula III can be selected which is specifically suited to each individual case, whether it be as an additive to other reaction media, as a reaction medium in pure form, or in a mixture.

Perfluoroalkanesulfonic acids preferably to be used according to the invention include, inter alia, $CF_3SO_3H$, $C_2F_5—SO_3H$,

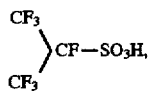

$n-C_4F_9—SO_3H$, $C_6F_{13}—SO_3H$, $CF_3—CFH—CF_2—SO_3H$, $CHF_2—CF_2—SO_3H$, $C_3F_7—CFH—CF_2—SO_3H$, $C_5F_{11}—CFH—CF_2—SO_3H$, $CFCl_2—CF_2—CFH—CF_2—SO_3H$.

Particular preference, among the compounds of the formula III, is given in the context of the invention to $CF_3SO_3H$, $CF_3—CFH—CF_2—SO_3H$ and/or $n-C_4F_9—SO_3H$.

The advantages associated with the invention may be at least partially achieved simply by adding the polyfluoroalkanesulfonic acids of the formula III to an otherwise conventional reaction medium for direct fluorination. A proportion of more than 50% by weight, based on the total weight of the reaction medium, is expedient in this case.

The advantages according to the invention appear particularly markedly, however, when the direct fluorination is carried out in polyfluoroalkanesulfonic acids of the formula III as reaction medium. Although in this case minor amounts of other solvents or diluents are not excluded, their addition is restricted to small proportions (<10% by volume).

In a particularly expedient process variant, only compounds of the formula III (either pure or in a mixture of two or more compounds coming under the formula III) are used.

In an advantageous modification of the process according to the invention, the process for preparing fluorinated aromatics further comprises diluting the compound to be fluorinated of the formula II with polyfluoroalkanesulfonic acids of the formula III as reaction medium, or dissolving it therein, and introducing gaseous fluorine into the reaction medium. This can proceed directly in molecular form, expediently, for better control of the reaction, the fluorine is passed together with an inert carrier gas through the reaction medium.

In this case the ratio of fluorine gas to carrier gas, depending on the sought-after purpose, can vary over a broad range of composition. Advantageously, the ratio of fluorine to carrier gas is between about 3 and 25 percent by volume.

Suitable carrier gases are, in principle, all gaseous substances which are inert to reaction partners. The use of nitrogen as carrier gas is particularly advantageous owing to its ready availability in sufficient purity.

The stoichiometric ratio of fluorine to aromatics is not, in the first place, particularly critical for the fluorination per se. However, the type and composition of the products obtained is, inter alia, a function of the amount of fluorine used.

In one variant, the process of the invention comprises compounds of the formula II being fluorinated, in which Z is H, and gaseous fluorine being passed into the reaction medium in a ratio of 1.1:1 to 2:1 mol based on the number of mols of the aromatic compound to be fluorinated, so that monofluorination predominates in the reaction occurring between aromatics and fluorine.

In an alternative process variant, compounds of the formula II are fluorinated, in which Z is H, and gaseous fluorine being introduced into the reaction medium in a ratio of 2.1:1 to 4:1 mol, based on the number of mols of the aromatic compound to be fluorinated, so that difluorination predominates in the reaction occurring between aromatics and fluorine.

The temperature during the direct fluorination is preferably in a range of about 0° to 30° C.

Temperatures of about 10° to 25° C. are particularly expedient. Very particularly preferably, the fluorination is simply carried out at a room temperature of about 25° C.

The yields of monofluoro derivatives which can be achieved by the invention are between about 60 and 90% by weight, in particular about 80% by weight. The conversion rate varies between 80 and 99%, based on the amount of the aromatic starting materials introduced into the reaction.

The invention also relates to the use of polyfluoroalkanesulfonic acids of the formula III $$CF_nH_{3-n}(CFY)_m\text{—}SO_3H \qquad (III)$$

in which m is 0 or a positive integer from the range 1 to 5, n is a positive integer from the range 1 to 3 and Y is F, Cl, H or RFY', where Y' is F, Cl or H and R is $C_{1-3}$-alkylene, linear or branched, which, if appropriate, can be partially fluorinated or else perfluorinated, in a reaction medium in the direct fluorination of aromatic compounds of the formula III

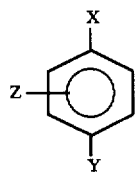

in which X is COOH, COOR, CONH$_2$, CONR$^1$R$^2$, CF$_3$, CN, CHO, NO$_2$ or NH$_2$, Y is F, Cl, OCH$_3$, OCF$_3$, OCCl$_3$, p-NO$_2$—C$_6$H$_4$, p-NO$_2$—C$_6$H$_4$—O or OH, and Z is H, F, Cl, CF$_3$, CCl$_3$ or OCH$_3$, where R, R$^1$ and R$^2$ independently of one another can be identical or different $C_1$-$C_6$-alkyl, linear or branched, and the alkyl radicals R, R$^1$ and R$^2$ can optionally be up to trisubstituted with halogen.

Very particular preference is given here to the use of the polyalkanesulfonic acids of the formula III not only in a reaction medium, but as reaction medium, which means without addition of further diluents or solvents.

The examples below serve to illustrate the subject-matter of the invention.

EXAMPLE 1

A solution of 0.1 mol of p-chloronitrobenzene in 50 ml of polyfluoroalkanesulfonic acid (CF$_3$—CFH—CF$_2$—SO$_3$H) was charged into a reactor suitable for direct fluorination. A stream of N$_2$ was passed through the solution for 15 min. A defined amount of F$_2$ was then added to the nitrogen stream, so that a 10–20% by volume mixture with the nitrogen resulted. The mixture of carrier gas and fluorine was conducted through the solution of the substrate in the reaction medium at a flow rate of about 10–20 ml/min. The mixture of nitrogen and fluorine was passed through the reaction medium until the amount of fluorine passed through corresponded to about 0.12 mol. The reaction mixture was then flushed for a further 20 min with pure nitrogen, in order to remove unconsumed residues of the F$_2$.

For the workup, the reaction mixture was poured into an excess of water and the solid constituents were filtered off, if necessary extracted with CH$_2$Cl$_2$ to recover liquid products, washed with water and dried. The resulting product mixture can be analyzed by GC, GCMS and $^{19}$F NMR. The products are further purified by recrystallization from suitable solvents or fractional distillation at atmospheric pressure or at reduced pressure.

The overall yield of aromatic products was 88% by weight.

The product composition was:

66% by weight of 3-fluoro-4-chloronitrobenzene,

33% by weight of 4-chloronitrobenzene and

1% by weight of 3,5-difluoro-4-chloronitrobenzene.

EXAMPLE 2

A solution of 0.1 mol of p-chloronitrobenzene in 50 ml of polyfluoroalkanesulfonic acid (CF$_3$—CFH—CF$_2$—SO$_3$H) was directly fluorinated as described in Example 1, with the difference that a mixture of nitrogen and fluorine was passed through the reaction medium until the amount of fluorine passed through corresponded to about 0.15 mol.

For the workup, the completely reacted reaction mixture was poured into an excess of water and the solid constituents were filtered off, if necessary extracted with CH$_2$Cl$_2$ to recover liquid products, washed with water and dried. The resulting product mixture can be analyzed by GC, GCMS and $^{19}$F NMR. The products are further purified by recrystallization from suitable solvents or fractional distillation at atmospheric pressure or at reduced pressure.

The overall yield of aromatic products was 91% by weight.

The product composition was:

78% by weight of 3-fluoro-4-chloronitrobenzene,

19% by weight of 4-chloronitrobenzene and

3% by weight of 3,5-difluoro-4-chloronitrobenzene.

Comparison example 2a as Example 2 with the difference that a solution of 0.05 mol of p-chloronitrobenzene in 50 ml of concentrated H$_2$SO$_4$ instead of polyfluoroalkanesulfonic acid (CF$_3$—CFH—CF$_2$—SO$_3$H) was directly fluorinated.

The overall yield of aromatic products was 75% by weight.

The product composition was:

63% by weight of 3-fluoro-4-chloronitrobenzene,

35% by weight of 4-chloronitrobenzene and

2% by weight of 3,5-difluoro-4-chloronitrobenzene.

EXAMPLE 3

A solution of 0.1 mol of p-chloronitrobenzene in 50 ml of polyfluoroalkanesulfonic acid was directly fluorinated as described in Example 1, with the difference that a mixture of nitrogen and fluorine was passed through the reaction medium until the amount of fluorine passed through corresponded to about 0.2 mol.

For the workup, the completely reacted reaction mixture was poured into an excess of water and the solid constituents were filtered off, if necessary extracted with CH$_2$Cl$_2$ to recover liquid products, washed with water and dried. The resulting product mixture can be analyzed by GC, GCMS and $^{19}$F NMR. The products are further purified by recrystallization from suitable solvents or fractional distillation at atmospheric pressure or at reduced pressure.

The overall yield of aromatic products was 87% by weight.

The product composition was:

85% by weight of 3-fluoro-4-chloronitrobenzene,

3% by weight of 4-chloronitrobenzene and

12% by weight of 3,5-difluoro-4-chloronitrobenzene.

EXAMPLE 4

A solution of 0.1 mol of p-fluoronitrobenzene in 50 ml of polyfluoroalkanesulfonic acid (n-C$_4$F$_9$—SO$_3$H) was charged into a reactor suitable for direct fluorination and fluorinated as described in Example 1. In this case, the mixture of carrier gas and fluorine was passed through the reaction medium until the amount of fluorine passed through corresponded to about 0.12 mol.

For the workup, the product was distilled off under reduced pressure (0.01 mbar) and purified by fractional distillation in vacuo.

The overall yield of aromatic products was 87% by weight.

The product composition was:

75% by weight of 3,4-difluoronitrobenzene,

21% by weight of 4-fluoronitrobenzene and

4% by weight of 3,4,5-trifluoronitrobenzene.

EXAMPLE 5

A solution of 0.1 mol of p-fluoronitrobenzene in 50 ml of polyfluoroalkanesulfonic acid (n-$C_4F_9$—$SO_3H$) was charged into a reactor suitable for direct fluorination and fluorinated as described in Example 1. In this case, the mixture of carrier gas and fluorine was passed through the reaction medium until the amount of fluorine passed through corresponded to about 0.18 mol.

For the workup, the product was distilled off under reduced pressure (0.01 mbar) and purified by fractional distillation in vacuo.

The overall yield of aromatic products was 90% by weight.

The product composition was:

88% by weight of 3,4-difluoronitrobenzene,

2% by weight of 4-fluoronitrobenzene and

10% by weight of 3,4,5-trifluoronitrobenzene.

Comparison example 5a as Example 5 with the difference that a solution of 0.05 mol of p-fluoronitrobenzene in 50 ml of concentrated $H_2SO_4$ was directly fluorinated.

The overall yield of aromatic products was 76% by weight.

The product composition was:

71% by weight of 3,4-difluoronitrobenzene,

19% by weight of 4-fluoronitrobenzene and

10% by weight of 3,4,5-trifluoronitrobenzene.

EXAMPLE 6

A solution of 0.1 mol of 2,4-difluorobenzoic acid in 50 ml of polyfluoroalkanesulfonic acid (n-$C_4F_9$-$SO_3H$) was charged into a reactor suitable for direct fluorination and fluorinated as described in Example 1. In this case, the mixture of carrier gas and fluorine was passed through the reaction medium until the amount of fluorine passed through corresponded to about 0.20 mol.

For the workup, the reaction medium was distilled off under reduced pressure (0.01 mbar) and the remaining product was purified by crystallization from methanol.

The overall yield of aromatic products was 91% by weight.

The product composition was:

75% by weight of 2,4,5-trifluorobenzoic acid and

25% by weight of 2,3,4-trifluorobenzoic acid.

EXAMPLE 7

A solution of 0.1 mol of p-nitrotrifluoroanisole in 50 ml of polyfluoroalkanesulfonic acid (n-$C_4F_9$—$SO_3H$) was charged into a reactor suitable for direct fluorination and fluorinated as described in Example 1. In this case, the mixture of carrier gas and fluorine was passed through the reaction medium until the amount of fluorine passed through corresponded to about 0.18 mol.

For the workup, the product was purified by fractional distillation in vacuo.

The overall yield of aromatic products was 93% by weight.

The product composition was:

92% by weight of 2-fluoro-4-nitrotrifluoroanisole,

6% by weight of 4-nitrotrifluoroanisole and

2% by weight of 2,5-difluoro-4-nitrotrifluoroanisole.

EXAMPLE 8

A solution of 0.1 mol of p-nitrophenol in 50 ml of polyfluoroalkanesulfonic acid ($CF_3$—$SO_3H$) was charged into a reactor suitable for direct fluorination and fluorinated as described in Example 1. In this case, the mixture of carrier gas and fluorine was passed through the reaction medium until the amount of fluorine passed through corresponded to about 0.12 mol.

For the workup, the reaction medium was distilled off under reduced pressure (0.1 mbar) and the remaining product was purified by crystallization.

The overall yield of aromatic products was 89% by weight.

The product composition was:

94% by weight of 2-fluoro-4-nitrophenol, 5 2% by weight of 4-nitrophenol and

4% by weight of 2,5-difluoro-4-nitrophenol.

EXAMPLE 9

A solution of 0.1 mol of p-fluoronitrobenzene in 50 ml of polyfluoroalkanesulfonic acid ($CF_3$—$SO_3H$) was charged into a reactor suitable for direct fluorination and fluorinated as described in Example 1. In this case, the mixture of carrier gas and fluorine was passed through the reaction medium until the amount of fluorine passed through corresponded to about 0,3 mol. For the workup, the completely reacted reaction mixture was poured into an excess of water, the products extracted with $CH_2Cl_2$, washed with water and dried. The resulting products were analyzed by GC and 19F NMR. The products were further purified by fractional distillation under reduced pressure.

The overall yield of aromatic products was 63% by weight.

The product composition was:

3% by weight of 4-fluoronitrobenzene,

20% by weight 3,4-difluoronitrobenzene,

70% by weight 3,4,5-trifluoronitrobenzene, and 7% by weight 1,4,5-trifluoronitrobenzene.

The table below gives a summary of the substrates used in the examples 1 to 8, the amount of fluorine used for the direct fluorination, the yield of total product and the composition of the respective aromatic products obtained.

Further advantages and embodiments of the invention are given by the patent claims below.

| Example/ Comp. Example | Substrate (0.1 mol) | Reaction medium | Amount of fluorine (mol) | Yield (% by weight) | Product composition | | |
|---|---|---|---|---|---|---|---|
| 1 | 4-chloronitrobenzene | CF₃—CHF—CF₂—SO₃H | 0.12 | 88 | 2-fluoro-4-chloro-nitrobenzene 66% | 4-chloronitrobenzene 33% | 2,6-difluoro-4-chloronitrobenzene 1% |
| 2 | 4-chloronitrobenzene | CF₃—CHF—CF₂—SO₃H | 0.15 | 91 | 78% | 19% | 3% |
| 2a | | H₂SO₄ | 0.15 | 75 | 63% | 35% | 2% |
| 3 | 4-chloronitrobenzene | CF₃—CHF—CF₂—SO₃H | 0.20 | 87 | 85% | 3% | 12% |
| 4 | 4-fluoronitrobenzene | n-C₄F₉—SO₃H | 0.12 | 87 | 75% | 21% | 4% |
| 5 | 4-fluoronitrobenzene | n-C₄F₉—SO₃H | 0.18 | 90 | 88% | 2% | 10% |
| 5a | 4-fluoronitrobenzene | H₂SO₄ | 0.18 | 76 | 71% | 19% | 10% |

-continued

| Example/ Comp. Example | Substrate (0.1 mol) | Reaction medium | Amount of fluorine (mol) | Yield (% by weight) | Product composition | | |
|---|---|---|---|---|---|---|---|
| 6 | 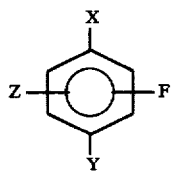 | n-C$_4$F$_9$—SO$_3$H | 0.20 | 91 | COOH, F, F, F (75%) | COOH, F, F, F (25%) | |
| 7 | 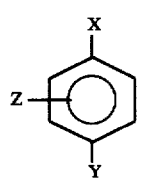 | n-C$_4$F$_9$—SO$_3$H | 0.18 | 93 | OCF$_3$, F, NO$_2$ (92%) | OCF$_3$, NO$_2$ (6%) | OCF$_3$, F, F, NO$_2$ (2%) |
| 8 | | CF3—SO3H | 0.12 | 89 | 94% | 2% | 4% |

We claim:

1. A process for preparing fluorinated aromatic compounds of the formula I $$\begin{array}{c} X \\ Z - \bigcirc - F \\ Y \end{array}$$

in which

X is COOH, COOR, CONH$_2$, CONR$^1$R$^2$, CF$_3$, CN, CHO, NO$_2$ or NH$_2$,

Y is F, Cl, OCH$_3$, OCF$_3$, OCCl$_3$, p-NO$_2$—C$_6$H$_4$, p-NO$_2$—C$_6$H$_4$—O or OH, and Z is H, F, Cl, CF$_3$, CCl$_3$ or OCH$_3$, where R, R$^1$ and R$^2$ independently of one another can be identical or different C$_1$-C$_6$-alkyl, linear or branched, and the alkyl radicals R, R$^1$ and R$^2$ can optionally be up to trisubstituted with halogen, by reacting aromatic compounds of the formula II $$\begin{array}{c} X \\ Z - \bigcirc \\ Y \end{array}$$

in which

X, Y and Z have the meaning specified for formula I, with fluorine in a reaction medium, which comprises carrying out the direct fluorination in a reaction medium containing polyfluoroalkanesulfonic acids of the formula III $$CFnH_{3-n}(CFY)_m—SO_3H \qquad (III)$$

in which m is 0 or a positive integer from the range 1 to 5, n is a positive integer from the range 1 to 3 and Y is F, Cl, H or RFY', where Y' is F, Cl or H and R is C$_{1-3}$-alkylene, linear or branched, which, if appropriate, can be partially fluorinated or else perfluorinated.

2. The process as claimed in claim 1, wherein the direct fluorination is carried out in polyfluoroalkanesulfonic acids of the formula III as reaction medium.

3. The process as claimed in claim 1, wherein the compound to be fluorinated of the formula II is diluted with polyfluoroalkanesulfonic acids of the formula III as reaction medium, or dissolved therein, and gaseous fluorine is introduced into the reaction medium.

4. The process as claimed in claim 3, wherein the fluorine is passed together with an inert carrier gas through the reaction medium.

5. The process as claimed in claim 4, wherein the ratio of fluorine to carrier gas is between about 3 and 25 percent by volume.

6. The process as claimed in claim 5, wherein the carrier gas used is nitrogen.

7. The process as claimed in claim 1, wherein CF$_3$SO$_3$H, CF$_3$—CFH—CF$_2$—SO$_3$H and/or n-C$_4$F$_9$—SO$_3$H is used as reaction medium.

8. The process as claimed in claim 1, wherein compounds of the formula II are fluorinated in which Z is H, and gaseous fluorine is passed into the reaction medium in a ratio of 1.1:1 to 2:1 mol, based on the number of moles of the aromatic compound to be fluorinated, so that monofluorination predominates in the reaction occurring between aromatics and fluorine.

9. The process as claimed in claim 1, wherein compounds of the formula II are fluorinated in which Z is H, and gaseous fluorine is introduced into the reaction medium in a ratio of 2.1:1 to 4:1 mol, based on the number of moles of the aromatic compound to be fluorinated, so that difluorination predominates in the reaction occurring between aromatics and fluorine.

10. The process as claimed in claim 1, wherein the direct fluorination is carried out at temperatures between about 0° and 30° C.

11. The process as claimed in claim 10, wherein the fluorination is carried out at a room temperature of about 25° C.

12. A reaction medium comprising a polyfluoroalkanesulfonic acid of formula III for direct fluorination of aromatic compounds of formula II, wherein formula III is:

$$CF_nH_{3-n}(CFY)_m-SO_3H \qquad (III)$$

in which m is 0 or a positive integer from the range 1 to 5, n is a positive integer from the range 1 to 3, and Y is F, Cl, H or RFY', where Y' is F, Cl or H and R is $C_{1-3}$-alkylene, linear or branched, which, if appropriate, can be partially fluorinated or else perfluorinated, and formula II is:

(II)

in which

X is COOH, COOR, $CONH_2$, $CONR^1R^2$, $CF_3$, CN, CHO, $NO_2$ or $NH_2$,

Y is F, Cl, $OCH_3$, $OCF_3$, $OCCl_3$, p-$NO_2$—$C_6H_4$, p-$NO_2$—$C_6H_4$—O or OH, and Z is H, F, Cl, $CF_3$, $CCl_3$ or $OCH_3$, Where R, $R^1$ and $R^2$ independently of one another can be identical or different $C_1$-$C_6$-alkyl, linear or branched, and the alkyl radicals R, $R^1$ and $R^2$ can optionally be up to trisubstituted with halogen.

13. A method for direct fluorination of aromatic compounds of formula II,

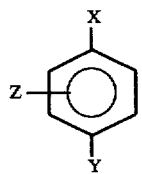

(II)

in which x is COOH, COOR, $CONH_2$, $CONR^1R^2$, $CF_3$, CN, CHO, $NO_2$ or $NH_2$, Y is F, Cl, $OCH_3$, $OCF_3$, $OCCl_3$, p-$NO_2$—$C_6H_4$, p-$NO_2$—$C_6H_4$—O or OH, and Z is H, F, Cl, $CF_3$, $CCl_3$ or $OCH_3$, Where R, $R^1$ and $R^2$ independently of one another can be identical or different $C_1$-$C_6$-alkyl, linear or branched, and the alkyl radicals R, $R^1$ and $R_2$ can optionally be up to trisubstituted with halogen, which comprises:

diluting a compound to be fluorinated in formula II with a reaction medium comprising polyfluoroalkanesulfonic acid of formula III, $$CF_nH_{3-n}(CFY)_m-SO_3H \qquad (III)$$

in which m is 0 or a positive integer from the range 1 to 5, n is a positive integer from the range 1 to 3, and Y is F, Cl, H or RFY', where Y' is F, Cl or H and R is $C_{1-3}$-alkylene, linear or branched, which, if appropriate, can be partially fluorinated or else perfluorinated, and introducing gaseous fluorine into the reaction medium.

* * * * *